United States Patent
Wicking et al.

(10) Patent No.: US 11,478,519 B2
(45) Date of Patent: Oct. 25, 2022

(54) NUTRITIONAL SUPPLEMENT CONTAINING IRON

(71) Applicant: CURA GLOBAL HEALTH (BVI) LIMITED, Tortola (VG)

(72) Inventors: J. Bruce Wicking, Ames, IA (US); Yilin Bian, Ames, IA (US)

(73) Assignee: Cura Global Health (BVI) Limited, Tortola (VG)

(*) Notice: Subject to any disclaimer, the term of this patent is extended or adjusted under 35 U.S.C. 154(b) by 6 days.

(21) Appl. No.: 16/557,293

(22) Filed: Aug. 30, 2019

(65) Prior Publication Data

US 2020/0030393 A1 Jan. 30, 2020

Related U.S. Application Data

(62) Division of application No. 14/425,493, filed as application No. PCT/AU2013/001028 on Sep. 10, 2013, now abandoned.

(Continued)

(51) Int. Cl.
| | |
|---|---|
| *A61K 36/062* | (2006.01) |
| *A23L 5/00* | (2016.01) |
| *A23L 31/00* | (2016.01) |
| *C12N 1/14* | (2006.01) |
| *A23L 33/16* | (2016.01) |
| *A23P 10/20* | (2016.01) |
| *A23P 10/40* | (2016.01) |

(Continued)

(52) U.S. Cl.
CPC .............. *A61K 36/062* (2013.01); *A23L 2/52* (2013.01); *A23L 5/00* (2016.08); *A23L 31/00* (2016.08); *A23L 33/16* (2016.08); *A23P 10/20* (2016.08); *A23P 10/30* (2016.08); *A23P 10/40* (2016.08); *A61K 33/26* (2013.01); *C12N 1/14* (2013.01); *A23L 7/00* (2016.08); *A23V 2002/00* (2013.01)

(58) Field of Classification Search
CPC ......... A61K 36/062; A61K 33/26; A23L 5/00; A23L 31/00; A23L 33/16; A23L 2/52; A23P 10/20; A23P 10/30; A23P 10/40
See application file for complete search history.

(56) References Cited

U.S. PATENT DOCUMENTS

| | | |
|---|---|---|
| 2006/0134227 A1 | 6/2006 | Bortz |
| 2007/0190209 A1 | 8/2007 | Sinnot |

(Continued)

FOREIGN PATENT DOCUMENTS

| | | |
|---|---|---|
| CN | 102356829 | 2/2012 |
| JP | S55-36314 B2 | 9/1980 |

(Continued)

OTHER PUBLICATIONS von der Osten et al, Design of a defined medium for growth ofCorynebacteriumglutamicum in which citrate facilitates iron uptake, 1989, Biotechnology Letters, 11(1): 11-16 (Year: 1989).*

(Continued)

*Primary Examiner* — Sharmila G Landau
*Assistant Examiner* — Stephanie A McNeil
(74) *Attorney, Agent, or Firm* — Barnes & Thornburg LLP; Alice O. Martin

(57) ABSTRACT

A nutritional supplement containing fungal biomass having at least 100 mg/kg iron and processes for producing the nutritional supplement using filamentous fungi are described.

16 Claims, 3 Drawing Sheets

Related U.S. Application Data

(60) Provisional application No. 61/699,623, filed on Sep. 11, 2012.

(51) Int. Cl.
  *A23P 10/30* (2016.01)
  *A23L 2/52* (2006.01)
  *A61K 33/26* (2006.01)
  *A23L 7/00* (2016.01)

(56) References Cited

U.S. PATENT DOCUMENTS

| | | | |
|---|---|---|---|
| 2010/0196994 A1 | 8/2010 | van Leeuwen et al. | |
| 2012/0208893 A1 | 8/2012 | Bolster | |

FOREIGN PATENT DOCUMENTS

| | | |
|---|---|---|
| JP | S57-68783 A | 4/1982 |
| JP | 2006199641 | 8/2006 |
| KR | 20090066410 | 6/2009 |
| RU | 2422043 | 6/2011 |

OTHER PUBLICATIONS

Znad et al, Production of gluconic acid from glucose by Aspergillus niger: growth and non-growth conditions, 2004, Process Biochemistry, 39: 1341-1345 (Year: 2004).*
U.S. Appl. No. 14/425,493, filed Mar. 3, 2015.
Bhalia et al., 2009, Microorganisms for food and feed, 1-63 (Year: 2009).
Extended European Search Report issued in App. No. EP13837585.2 (dated 2016).
Office Action issued in app. No. JP 2015-530243 (dated Apr. 17, 2017).
Office Action issued in App. No. CN2013800472379 (dated Nov. 23, 2017).
Paknikar et al., Bioremediation of Metalliferous Wastes and Products using Inactivated Microbial Biomass, 2003, Indian Journal of Biotechnology, 2:426-443.
Price et al., "*Aspergillus niger* absorbs copper and zinc from swine wastewater," 77(1):41-49 (2001). Abstract.
Search Report issued in Int'l App. No. PCT/AU2013/001028 (dated 2013).
Szczodrak et al., "Effect of Iron on The Activity of Aconitate Hydratase And Synthesis of Citric-Acid By Aspergillus-Niger," XP002754501, Database accession No. PREV198681061911.
XP002754499, CN 102356829 A (Hunan Chuangxin Biotechnology Co LTD) Feb. 22, 2012.
XP002754500, KR 2009 0066410 A (B&C Biopharm Co L To) Jun. 24, 2009.

* cited by examiner

NUTRITIONAL SUPPLEMENT CONTAINING IRON

CROSS REFERENCE TO RELATED APPLICATIONS

This application is a Divisional of U.S. application Ser. No. 14/425,493, filed Mar. 3, 2015, which is a U.S. nationalization under 35 U.S.C. § 371 of International Application No. PCT/AU2013/001028, filed Sep. 10, 2013, which claims the benefit of priority under 35 U.S.C. § 119(e) to U.S. Provisional Patent Application No. 61/699,623, filed Sep. 11, 2012. The disclosures set forth in the referenced applications are incorporated herein by reference in their entireties.

TECHNICAL FIELD

The technology relates to nutritional supplements containing iron and processes for making the supplements using filamentous fungi.

BACKGROUND

Based on a report by the World Health Organization (WHO) on global anemia, "anemia is a public health problem that affects populations in both rich and poor countries," in particular pregnant women, non-pregnant women of reproductive age, and preschool-age children. The most significant contributor to the onset of anemia is iron deficiency anemia (IDA). It has been estimated that over 1 billion people (approximately 15% of the global population) suffer from IDA. Additionally 1 billion people suffer from iron deficiency (ID) or iron depletion.

Globally, the prevalence of IDA has either remained stagnant or slightly increased over the last three decades. While the prevalence of other malnutrition disorders has progressively declined, ID and IDA and the associated detrimental effects have persisted.

Iron is essential to most life because it is an integral part of many proteins and enzymes that maintain good health. In humans, iron is an essential component of the red blood cells involved in oxygen transport, cell growth and other functions. Generally, ID limits oxygen delivery to the cell, resulting in fatigue, poor work performance and decreased disease immunity. But in children aged 0-5 years, ID impairs physical and cognitive development and thus may persist into adulthood. In pregnancy, IDA can result in 20-30% of maternal deaths, premature births and infant loss.

Currently, there are four types of major efforts to combat ID/IDA recommended by the WHO: food fortification, supplementation, education, and new plant breeding programs. The fortification and supplementation strategies, generally have a fast and direct impact on the ID/IDA problem in a given population group.

There are three major types of iron in human nutritional applications and they are listed in Table 1. Both heme iron and non-heme-iron are derived from food sources. However, the non-heme iron, mostly from cereal and beans, is poorly absorbed due to a high phytate content. Apart from improving overall nutrition, the major effort to combat ID/IDA rests upon iron supplements and fortification in food, particularly in developing countries where heme iron sources are scarce.

TABLE 1

Major types of iron that are considered important in human nutritional applications

| Type | Major Source | Examples |
|---|---|---|
| Heme Iron | Hemoglobin | Animal livers, red meat, poultry, and seafood |
| Non-Heme Iron | Plant Based Food | Lentils, grains and some vegetables |
| Inorganic Salt/Iron Supplements | Ferrous Salts | Ferrous sulfate, ferrous fumarate, ferrous citrate, ferrous gluconate, ferric ammoniums citrate, ferrous citrate and ethylenediaminetetraacetic acid (EDTA) iron |

Soluble compounds of iron salt, such as highly absorbable ferrous sulfate, are desirable as iron supplements but cannot be used in many fortified foods due to sensory issues. Other forms such as ferrous fumarate can be microencapsulated and added to semi-liquid food but costs are significantly higher. Iron fortification of food is the preferred method to provide iron to regions of the world. There are many types of iron products used in fortified food, successful forms include ferrous sulfate or NAFeEDTA fortified fish sauce and soy sauce with ascorbic acid. However, the impact of fortification on the prevalence of ID at the population level has not proven successful. One of the reasons is due to iron enhancers vs inhibitors in the food delivery vehicles, for example cereal flours. In contrast to iodine and vitamin A, the iron fortification and supplements need different products to fit into many food systems. Therefore, more non-heme iron products in organic form are needed to meet demand across diverse dietary situations.

In U.S. Pat. No. 8,481,295 (van Leeuwen) filamentous fungi have been cultivated on alcohol fermentation stillage to remove organic waste material for water recycling at a corn-ethanol dry-mill production plant and obtain fungal biomass for animal feed and other uses. Such fungal biomass would have a low iron content and not enough to be used as a mineral supplement. Because the current corn-ethanol dry-mill production is an industrial process and not a food process the fungal biomass is not approved by US Food and Drug Administration (FDA) for direct human consumption.

The present inventors have now found that filamentous fungi can be cultivated on an agricultural by-product or a food processing by-product and harvested to obtain a nutritional product high in iron.

SUMMARY

Nutritional supplements containing iron and methods for forming nutritional supplements containing iron are disclosed.

In one embodiment, there is provided a nutritional supplement comprising:

fungal biomass having at least about 100 mg/kg iron.

Preferably the nutritional supplement contains from about 200 to 40000 mg/kg iron.

The nutritional supplement containing iron may include diluents or other co-ingredients such as selenium and zinc. For example, the supplement may contain selenium from 10 to 400 mg/kg; and zinc from 20 to 20,000 mg/kg.

The nutritional supplement containing iron may be formulated as a powder, solution, drink, capsule, tablet, caplet. The powdered form of product can also be added to food and used as a food fortification ingredient. The fortification of food includes, but is not limited to condiments, salt, baby formula, and flours of wheat, corn and beans.

An advantage of the nutritional supplement is that it contains natural organic iron derived from the by-products. The nutritional supplement may be formulated to further contain phytase and other enzymes naturally produced by the filamentous fungi.

The nutritional supplement may contain additional inorganic iron salts or other high iron compounds added during growth of the filamentous fungi. Examples include ferrous sulfate, ferrous fumarate, ferrous citrate, ferrous gluconate, ferric ammoniums citrate, ferrous citrate and EDTA iron.

In one embodiment, there is provided a process for forming a nutritional supplement containing iron, the process comprising:
  culturing filamentous fungi in an agricultural by-product or a food processing by-product to accumulate iron present in the agricultural or food processing by-product in the filamentous fungi; and
  harvesting the filamentous fungi to obtain a nutritional supplement containing fungal biomass having at least about 100 mg/kg iron.

Preferably the filamentous fungi is selected from *Aspergillus oryzae* or *Aspergillus niger*.

The agricultural by-product can be from waste derived from corn, wheat, sugar beet, cane sugar, soybean, stillage and solid waste from alcohol production. Examples of such products are sugar cane and beet pulps, soybean hull, soybean process whey, wheat hull, spent grain and stillage. Preferably the agricultural by-product is condensed corn soluble (Syrup), corn, wheat and soybean process by-products. More preferably, the agricultural by-product is Syrup.

Preferably the food processing by-product is selected from corn steeping liquor, corn stillage, soybean whey, sugar cane and beet molasses, soybean hull and wheat bran and wheat hull.

Additional growth media can be provided to the agricultural by-product or a food processing by-product to assist growth and accumulation of iron by the filamentous fungi during culture.

Additional inorganic iron salts and other high iron compounds such as ferric sulfate, ferrous sulfate, ferric ammonium citrate, ferrous citrate, but not limited to these salts maybe added during growth of the filamentous fungi to further increase iron content of the nutritional supplement.

The nutritional supplement may further include other minerals such as selenium and zinc or other minerals such as magnesium, calcium and chromium. To achieve further mineral supplementation, selenium and zinc compounds may be added to the culture. Suitable compounds include sodium selenite, zinc sulfate, calcium sulphate, chromium chloride, and magnesium sulphate.

The nutritional supplement may further include selenium and zinc. Preferably the nutritional supplement contains selenium from 10 to 400 mg/kg; and zinc from 20 to 20,000 mg/kg.

Additional culture media or nutrients may be provided to assist in growth of the filamentous fungi. Examples include yeast extract, ammonium salts, urea, and potassium phosphorus.

The filamentous fungi may be cultured in any suitable environment such as fermentation vessels used in both solid and liquid fermentations.

Culture of the filamentous fungi may be carried out at room temperature or elevated temperatures such as 25 to 55° C.

The filamentous fungi can be harvested by any suitable means. Examples include filtration, such as filter press, belt press; centrifugation, such as decanter, drying, such as rotary drier, steam drier. The drying temperature is typically lower than about 90° C. to avoid any unwanted heat damage of the product.

The harvested filamentous fungi may be further processed to form the nutritional supplement containing iron. Further processing may include separating, crushing, grinding, fractionation, extraction, washing with cold and hot water to remove excess salts, or mild acid with pH of 2 or alkaline wash with pH of 9-10 to remove other soluble compounds.

The nutritional supplement contains at least about 200 mg/kg iron. Preferably the nutritional supplement contains from about 200 to 40000 mg/kg iron. The iron content can be higher than 40000 mg/kg, but the yield of fungi biomass may be reduced and may not be economical in practice.

The nutritional supplement containing iron may include diluents or other co-ingredients such as selenium and zinc. For example, the supplement may contain selenium from 10 to 400 mg/kg; and zinc from 20 to 20,000 mg/kg.

The nutritional supplement may contain additional inorganic iron salts or other high iron compounds added during growth of the filamentous fungi. Examples include ferrous sulfate, ferrous fumarate, ferrous citrate, ferrous gluconate, ferric ammoniums citrate, ferrous citrate and EDTA iron.

The nutritional supplement may be formulated for human or animal use.

In another embodiment, the technology relates to a nutritional supplement containing iron produced by the process described.

In a further embodiment, the technology relates to a nutritional supplement containing iron derived or obtained from filamentous fungi cultured in an agricultural by-product or a food processing by-product.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

In order that the present technology may be more clearly understood, preferred embodiments will be described with reference to the following drawings and examples.

DETAILED DESCRIPTION

Figure 1:
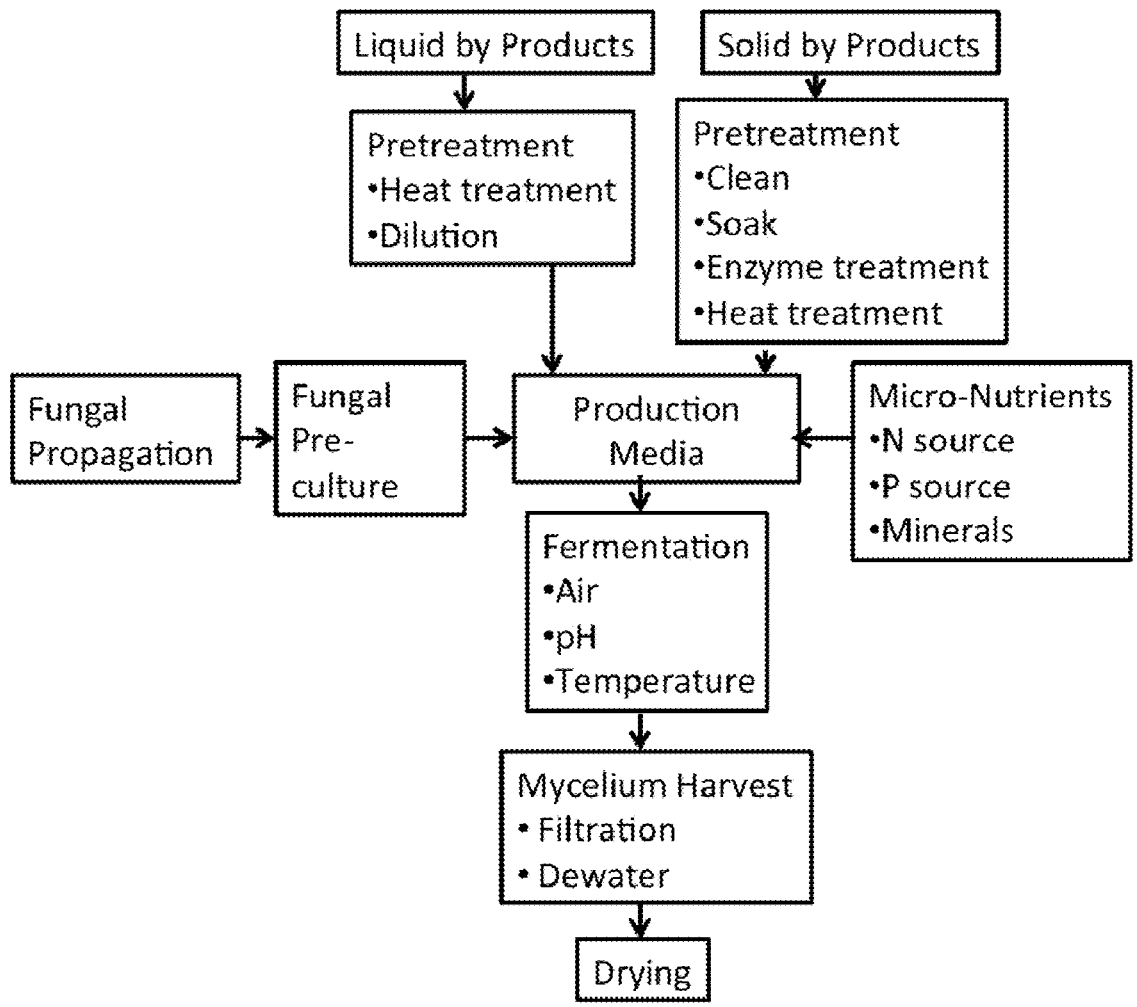
FIG. 1 is a schematic of a preferred process for the present technology.

Yeast has been reported to accumulate many microelements including iron on Yeast Extract Peptone Dextrose (YEPD) plates containing $FeSO_4$. Certain yeast strains can uptake iron to 25 mg per gram of cell and as high as 95% of this iron was considered as being an organic form in the cell structure. Yeast biomass enriched with iron is used as an animal feed supplement and is considered less toxic as compared to iron salt. In other non-yeast mycelia forming fungi, the $Fe3+$, $Fe2+$, $Mg2+$ and $Zn2+$ are able to stimulate glucan formation. However, the use of filamentous fungi to produce an iron enriched product has not been practiced. The fundamental difference between the current technology and the iron enrichment of yeast is the recognition by the present inventors that the filamentous fungi, such as *Aspergillus oryzae*, have the ability to accumulate organic iron from natural sources such as agricultural and food process wastes and by-products without iron fortification when such wastes and by-products are used as a growth media. There are many filamentous fungi that have Generally Recognized as Safe (GRAS) status, such as *Aspergillus oryzae* and *Aspergillus niger* that can be used in production of iron rich and enriched products. A further advantage is that the filamentous fungi product has no off flavor as compared to yeast products.

Agricultural by Product Selection and Pretreatment

There are many by-products produced from agricultural and food processing, but not all of them are naturally rich in iron. Table 2 lists some of the iron rich agricultural by products in North America that could be used for the production of iron rich fungal products. Other by products such wheat bran and hull, rice hull, sorghum hull and potato skin also have potential.

TABLE 2

Iron content of various agricultural processing by products

| By-Products | Source | Iron Content, mg/kg or L |
|---|---|---|
| Stillage or Syrup | Corn-Ethanol, dry-mill | 138 (dry based) |
| Cane Molasses | Sugar cane process | 249 (average) |
| Beet Molasses | Sugar beet process | 117 (average) |
| Citrus Molasses | Citrus juice process | 400 |
| Soybean Hull | Soybean process | 180-390 |

Even though some of the by-products are recognized as iron rich materials, many are not suitable for direct human consumption. Most iron in the grain by products is bound by phytate and as a result, the natural iron is not bioavailable to humans. The use of phytase to improve iron bioavailability in these products is well understood but the daily requirement is too large for direct use on the basis of improving iron status in humans. The present technology relates to the use of selected fungal species as the means to concentrate iron into an organic form suitable for animal or human consumption.

Before any by-product can be used in the production of the iron-fungal product, testing is preferably carried out for microbial spoilage, mycotoxins and heavy metal contamination. For liquid raw materials, dilution may be necessary as the optimal total solids for liquid fermentation of fungal species, such as *Aspergillus oryzae* or *Aspergillus niger* is about 3-10%. Dry raw materials may be ground, soaked or cooked to release natural iron and reduce anti-fermentation factors. To assist natural iron release from raw materials, enzymes, such as cellulase, hemicellulase and phytase, may be used during soaking and cooking. Multiple raw materials may be used at the same time depending upon availability and pricing.

Process

General steps of a preferred process using an agricultural by-product or a food processing by-product are set out in FIG. 1.

Fungal Strains

Strains of *Aspergillus oryzae* used were the same strains that are approved and employed commercially for soy sauce and miso manufacture, including *Aspergillus oryzae* 2355 and 40151 from Chinese Center of Industrial Culture Collection (CICC); *Aspergillus oryzae* 22787 from American Type Culture Collection (ATCC) and *Aspergillus niger*. var. 2206 and 10557 for citric acid production from CICC and *Aspergillus niger* 66876 for phytase production from ATCC.

Fungal Culture

Stains of *Aspergillus oryzae* and *Aspergillus niger* were cultured and maintained in media composed of ground whole corn, wheat bran, soybean hulls, molasses of beet, cane and fruits juice process by-product, and any other food process by-product consist of starch, sugar and protein. Such raw materials can be pretreated by enzymes, including amylases, gluco-amylases, phytase and protease. Inorganic iron salts were added to the fungal culture media, such inorganic iron salts include ferrous sulfate, ferrous fumarate, ferrous citrate, ferrous gluconate, ferric ammoniums citrate, ferrous citrate and ethylenediaminetetraacetic acid (EDTA) iron at concentration of 300-2000 mg of iron element per liter of media.

Fungal spores were prepared by inoculating a solid media, such as cooked rice, soybean, and sorghum and the combination of them with moisture of 40-70%. In 2-3 weeks, the spores germinated and were ready to be collected. The fungal spores were collected into sterilized distill water. The pre-cultures fermenters were prepared with 1-10% volume of the final production fermenters. The media for the pre-cultures can be the same as the production media as described above. Incubation for 18-28 hours of pre-culture fermentation time is suitable to generate healthy pre-cultures after the spores were introduced into the pre-culture media. The pre-culture is added to the production fermenter and fungus is allowed to grow to produce the desired fungal mass containing iron.

Apparatus

Large scale fermentation can be carried out in any suitable fermentation vessel or apparatus. For the iron enriched biomass production, the fermentation is preferably carried out under aerobic conditions for 48-72 hours. Sterilized or filtered air can be pumped into the fermenter at 0.5 to 1.0 vvm during the fermentation period to improve growth and yield. The culture is preferably agitated or stirred during fermentation. The combination of air, agitation and design of the fermentation vessel is well understood for commercial microbial culture.

Fungal Fermentation

Fermentation can be carried out for 48-72 hours or until cell autolysis begins at a temperature of 28-30° C. It will be appreciated that incubation times and temperature may vary depending on the fungus type and strain used.

Depending on the nutritional profile of the raw materials, other nutrients may be needed to supplement the growth media for an aerated fungal fermentation. These nutrients may include organic and inorganic nitrogen sources, phosphors source and micro minerals.

Production of Iron Enriched Fungal Products as an Iron Supplement

Fungi, including filamentous fungi, have the ability to further uptake relatively bio-unavailable and strongly cytotoxic iron. It should be noted that, direct supplementation of soluble inorganic iron salt in human diets can result in a cytotoxic reaction. Therefore, using fungi to uptake the inorganic iron salts and transform to an organic form may reduce the side effects of the direct consumption of iron salts.

Figure 2:
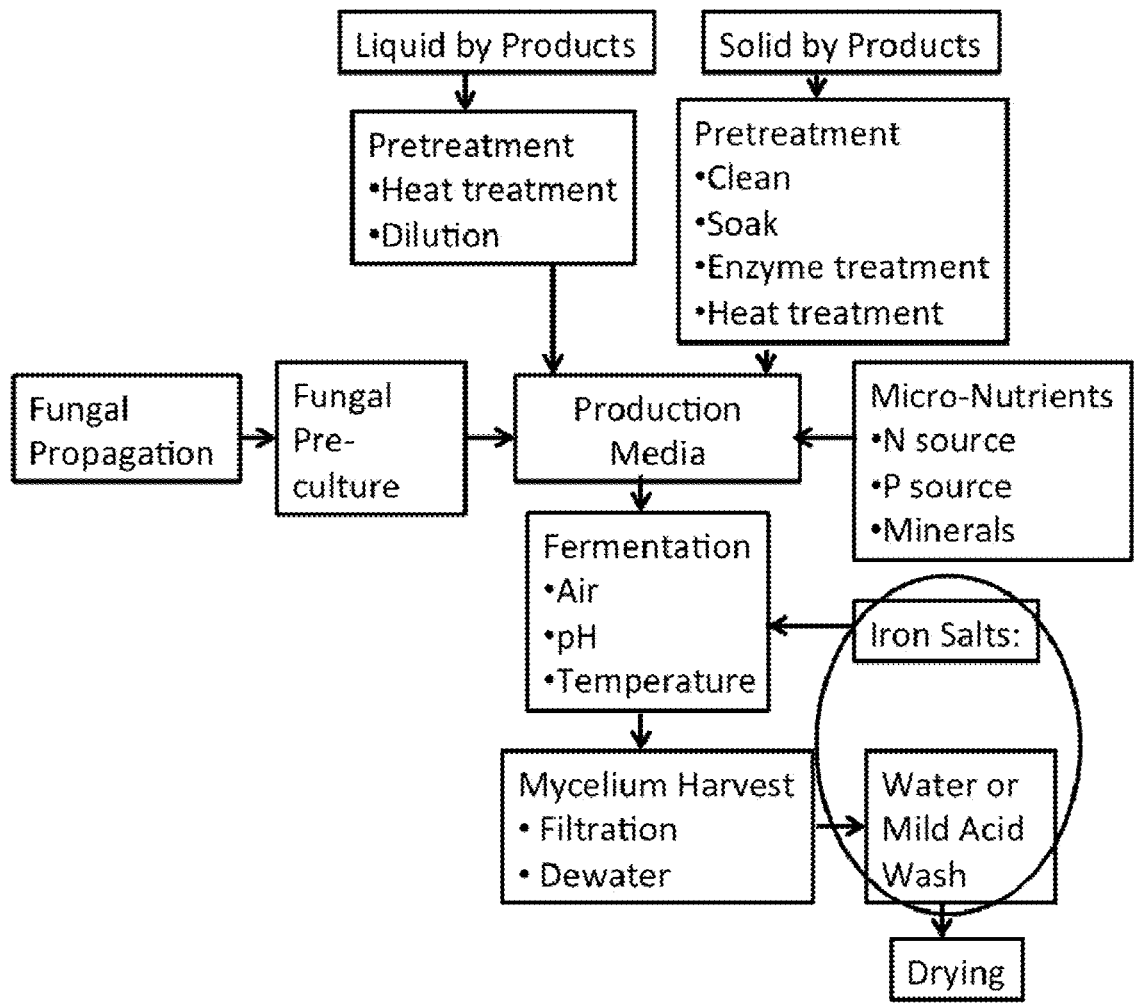
FIG. 2 is a schematic of another preferred process for the present technology.

Inorganic salts can be added during the fermentation. The common choice of iron salts includes ferric sulfate, ferrous sulfate, and ferric citrate. The inorganic iron is converted to an organic form by the fungi. To maximize the level of iron in the fungal product, a given iron salt can be incrementally fed during the fermentation. The dosing of iron salts depends on the type of salt used but the dosing level needs to not compromise the growth of fungi. After harvest, the fungal mycelium can be thoroughly washed to remove excess iron salts. A mild acid, pH 2-3, wash can be effective in this regard. Detailed steps of the process are described in FIG. 2.

Fungal Biomass Harvesting

After fermentation, fungal biomass containing iron can be harvested by a dewatering machine such as a centrifuge, belt press etc. Washing with water and/or mild acid such as hydrochloric acid 0.01 M can be used to remove inorganic iron residues. The iron enriched fungal product can then be dried at 60-80° C. using forced air, fluid bed dryer, etc. The final moisture of the product is preferably less than about 10%.

Formulation

For example, the compounds may be formulated for oral delivery. Non-limiting examples of particular formulation types include tablets, capsules, caplets, powders, granules, ampoules, vials, ready-to-use solutions or suspensions, drinks, and lyophilized materials. The solid formulations such as the tablets or capsules may contain any number of suitable acceptable excipients or carriers.

Products

The nutritional supplement comprises fungal biomass having at least about 100 mg/kg iron. The nutritional supplement typically contains from about 100 to 40000 mg/kg iron. The supplement can have at least about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, or 40000 mg/kg iron.

The nutritional supplement containing iron may also include diluents or other co-ingredients such as selenium and zinc. For example, the supplement may contain selenium from 10 to 400 mg/kg; and zinc from 20 to 20,000 mg/kg. The supplement may contain 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390 or 400 mg/kg selenium. The supplement may also contain 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, 10000, 11000, 12000, 13000, 14000, 15000, 16000, 17000, 18000, 19000 or 20000 mg/kg zinc.

The nutritional supplement containing iron may be formulated as a powder, solution, drink, capsule, tablet, caplet. The powdered form of product can also be added to food and used as a food fortification ingredient. The fortification of food includes, but is not limited to condiments, salt, baby formula, and flours of wheat, corn and beans.

An advantage of the nutritional supplement is that it contains natural organic iron derived from the by-products. The nutritional supplement may be formulated to further contain phytase and other enzymes naturally produced by the filamentous fungi.

The nutritional supplement may contain additional inorganic iron salts or other high iron compounds added during growth of the filamentous fungi. Examples include ferrous sulfate, ferrous fumarate, ferrous citrate, ferrous gluconate, ferric ammoniums citrate, ferrous citrate and EDTA iron.

The nutritional supplement can be formulated for human or animal use.

RESULTS

Example 1

Condensed corn distillers soluble (Syrup), a major by-product, is generated from the dry grind of corn to produce ethanol. The fermentation process converts corn starch to ethanol but leaves a major portion of non-starch nutrients, including iron from the corn, behind as stillage. The stillage is then concentrated to Syrup and is used primarily for animal feed.

Syrup has now been found to contain viable nutrients for the production of fungal biomass, such as *Aspergillus oryzae* and *Aspergillus niger*.

When media made of diluted Syrup (DS), fungal biomass and the residue liquid (SL) were analyzed for iron content, the results indicated that 86.8% of the natural iron in Syrup was concentrated by the fungi (Table 3). However, the other advantage of using Syrup verses thin stillage as compared to U.S. Pat. No. 8,481,295 (van Leeuwen) is that the Syrup is rich in phosphorous, when combined with other ingredient such as sugar, the fungal biomass can be increased as much as 30%.

TABLE 3

Iron balance *Aspergillus oryzae* from corn-ethanol thin stillage, in 1000 mL

|  |  | Measured | Calculated, in 1000 mL |
|---|---|---|---|
| Initial DS | Total solid (dry based) | 6% | 60.0 g |
|  | Iron content | 7.9 mg/L | 7.9 mg |
| Fungal Yield | Solid conversion (dry based) | 48% | 28.8 g |
|  | Iron content | 238 mg/kg | 6.85 mg/kg |
| Iron | Conversion |  | 86.8% |

Because the natural iron content in corn is determined by geographic location and weather conditions, iron content ranges from 1-100 mg/kg of dry corn. Consequently the iron residue in Syrup varies from corn-ethanol plant to plant. As a result, iron in fungal biomass produced from DS of different ethanol plants exhibited a range from 180 to 320 mg/kg.

To demonstrate that iron in fungal mycelium is bound to the cell wall, a hot water wash and a hexane extraction were conducted. The results indicated that by washing the product, the iron content in the final dry product actually increased due to the removal of soluble contents (Table 4). The results also indicated that the iron in the fungal product was bound to the cell structure. Since most corn-ethanol plants are practicing oil separation of corn oil from Syrup, it is preferable to use the reduced fat Syrup vs. original Syrup for culturing the fungi to obtain an iron-rich product.

TABLE 4

Hot water and hexane washes increased iron content in final fungal products

|  | Iron content |
| --- | --- |
| Initial DS | 8 mg/L |
| Unwashed | 251 mg/kg |
| Hot water wash for 2 hours | 274 mg/kg |
| Hexane extract for 6 hours | 303 mg/kg |

Based on the United State Department of Agricultural (USDA) nutrition data for foods (USDA National nutrient database for standard reference, release 17: Iron, Fe(mg) content of selected foods per common measure), not including iron enriched cereal and food products, the iron content in fungal biomass produced from corn-ethanol Syrup was higher than chicken livers on the same serving weight base and only 10.6% less than the highest iron content food, the canned clam. The iron content was higher than all the non-meat foods on an equal weight basis (Table 5). However, in the current commercial corn-ethanol operations, Syrup is not suited for direct human consumption. It would be necessary for the industry to upgrade the ethanol production facilities and chemicals and enzymes used to food grade quality before such by product can be used to produce iron supplement for human consumption. But iron rich product can be fed to livestock, and is especially suited to young swine (Kornievicz d, et. Al. 2007 Effect of dietary yeast enriched with Cu, Fe and Mn on digestibility of main nutrients and absorption of minerals by growing pigs. Am. J. Agril. Biol. Sci. 2(4), 267-275.

TABLE 5

Comparison of iron content in fungal products (an average of 250 mg/kg) to selected foods, not including iron enriched cereals and food products

| Description | Weight (g) | Common Measure | Iron Content per Measure (mg) | Fungal Iron on the Same Weight Basis (mg) |
| --- | --- | --- | --- | --- |
| Apricots, dried | 35 | 10 halves | 0.93 | 8.75 |
| Baking chocolate, unsweetened | 28.35 | 1 square | 4.93 | 7.06 |
| Baked beans, canned | 254 | 1 cup | 3.00 | 63.5 |
| Baked beans with pork, canned | 253 | 1 cup | 8.20 | 63.5 |
| Bread, whole-grain or 7 grain | 26 | 1 slice | 0.90 | 6.50 |
| Chicken liver | 19.6 | 1 liver | 2.28 | 4.90 |
| Lentils, mature seeds, cooked | 198 | 1 cup | 6.59 |  |
| Mollusks, clam, canned | 85 | 3 oz | 23.77 | 21.3 |
| Oat bran, raw | 94 | 1 cup | 5.09 | 23.5 |
| Potato, baked, skin | 58 | 1 skin | 4.08 | 14.5 |
| Spinach, cooked, drained | 180 | 1 cup | 6.43 | 45.0 |

Example 2

Although it has been reported that various yeasts can be used to generate iron enriched yeast products as a supplement, *Aspergillus oryzae* var. has not been used in producing iron-enriched products.

Ferric sulfate ($Fe_2(SO_4)_3 \cdot 2H_2O$) with $Fe^{3+}$ of 25.69%, was used as an inorganic salt to fortify corn-ethanol Syrup. The dose of iron was calculated as a concentration of iron elements rather than the concentration of salt; to enable comparison with the iron content in the fungal biomass. All fungal samples were thoroughly washed with deionizer water prior to testing by the ICP-OES method. The results (Table 6) indicated that the iron content in the fungal biomass increased dramatically as the $Fe^{3+}$ increased from 1-200 mg/L. Also interesting is that ferric sulfate was not toxic to *Aspergillus oryzae* at the given doses, but increased fungal yield numerically.

TABLE 6

Effect of adding ferric sulfate to Syrup to fungal iron content and yield.

| Media | Iron Salts | mg/L | Fungal Yield, g/L | Iron, (mg/kg) |
| --- | --- | --- | --- | --- |
| TS | Ferric Sulfate (Fe3+) | 0 | 18.74 | 257 |
|  |  | 100 | 20.56 | 2456 |
|  |  | 200 | 20.18 | 4626 |
| Corn Meal | Ferrous Sulfate (Fe2+) | 1000 | 17.5 | 13,500 |
|  |  | 2000 | 14.8 | 20,500 |

Figure 3:
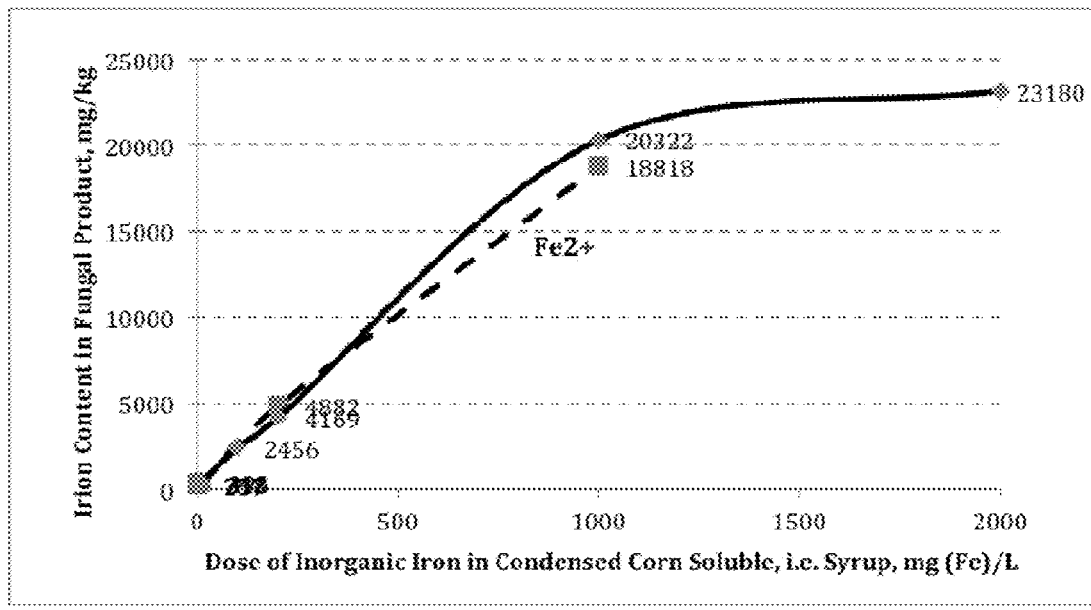
FIG. 3 shows results of the effect of addition of inorganic iron salts on fungal biomass iron content.
Figure 4:
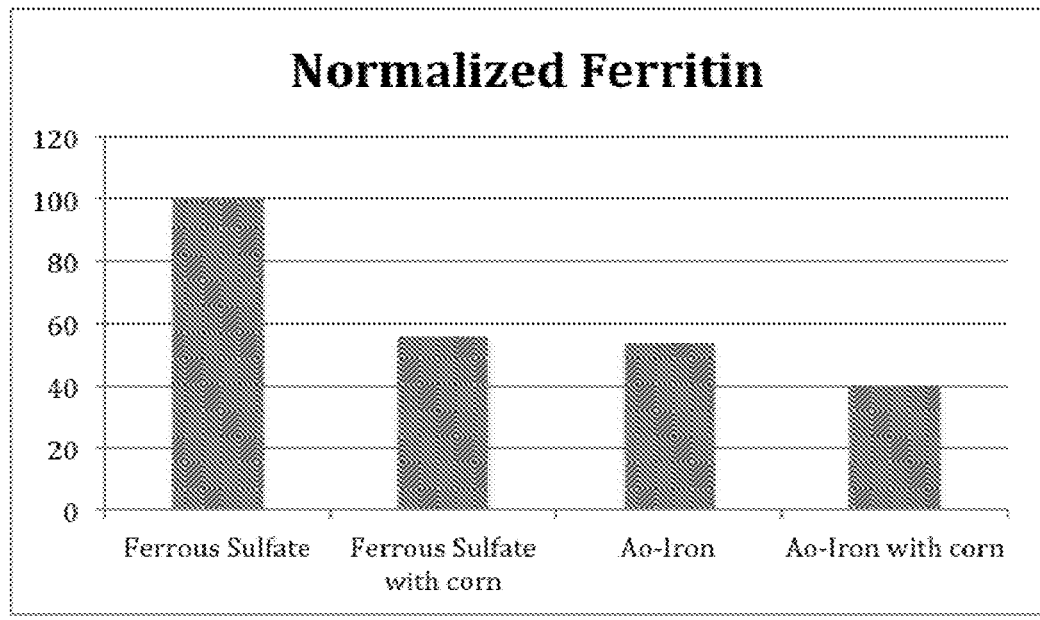
FIG. 4 shows results of Caco-2 Cell ferritin formation as % of ferrous sulfate.

In addition to ferric sulfate, ferrous sulfate ($FeSO_4 \cdot 7H_2O$) with $Fe^{2+}$ content of 20.14% was used as a comparison. FIG. 3 illustrates that *Aspergillus oryzae* could use both $Fe^{3+}$ and $Fe^{2+}$ inorganic salts and uptake both of them until the doses of iron reached over 1000 mg (Fe)/L. Both iron salts resulted in iron content in fungal biomass close to or over 20,000 mg/kg.

Even though ferrous sulfate is more water soluble and often used as an iron supplement, it did not appear to be different from ferric sulphate results. The mechanism of iron uptake by *Aspergillus oryzae* is capable of increasing iron content from 257 mg/kg to over 20,000 mg/kg; a 40 fold increase. When comparing these iron levels with the foods contained in Table 6, the fungal product is able to provide a very heavily enriched iron content product.

Example 3

It is preferable that an iron supplement has high iron content, but more importantly that such iron can be absorbed by humans. The iron enriched fungal product (Ao-Iron) was produced with the process illustrated in FIG. 2 using ingredients of corn, wheat bran and soybean hulls. The iron content in the final product ranged from 2-4% by the different combinations of the raw ingredients and fermentation optimization. The Ao-iron was ground to powder and subjected to an in vitro digestion/Caco-2 Cell Culture Model (Cell Test) detailed by Glahn (Glahn, R. P. et. al. 1998. Caco-2 cell ferritin formation predicts nonradiolabeled food iron availability in an In Vitro digestion/Caco-2 cell culture model). Cell culture, Caco-2 cells were obtained from the ATCC at passage 17, and used in experiments at passage 25-33. Cells were seeded at a density of $1.9 \times 10^5$ in collagen-treated 6-well plates. The cells were grown in Eagle's medium with 10% fetal calf serum and maintained at 37° C. in an environmental with 5% $CO_2$ The medium was changed every 2 days. In vitro digestion of the iron enriched fungal was following the steps also detailed by Glahn. The Cell Test measures the ferritin, an iron containing protein, formation in the cell incubated with the digested iron product; therefore has been used as a predictor of iron availability in humans. The basic steps of the Cell Test are enzymatic digestion (pepsin and pancreatin-bile) of the sample, culture on Caco-2 cell layer (from human large intestine) and measurement of ferritin (an iron containing protein) formation within the cell. Before the enzymatic digestion, the Ao-iron was washed with acidified water (pH=2) and EDTA to remove any residues of inorganic salt on the outside of the cell structures.

Because the Ao-iron has limited solubility in water and iron is bound to the fungal cell structure, the sample cannot be diluted like inorganic salts during the enzymatic digestion. A modified sample preparation procedure has been developed to be used in the Cell Test for the high iron content of organic materials. It was noted that the weight of such Ao-iron sample be kept low in a given digestion volume, in this case, it was 22.5 ml. Table 7 shows that an over loading of the sample during digestion led to low iron solubility. Such low solubility was due to incomplete digestion. However, when sample weight is ultra low, it is likely that an error may occur during weighing owing to the sensitivity of the weighing balance. It was determined that 0.005-0.01 grams of sample was optimal for the digestion volume of 20-25 ml. A larger sample size can be used but the enzyme dose during the digestion must also be adjusted.

TABLE 7

Effect of sample loading during enzymatic digestion on the solubility of iron

| Sample | Weight of Sample, g | Dilution Factor, times | Iron Solubility, % |
|---|---|---|---|
| Ferrous Sulfate | 0.095 | 100 | 140 |
| Iron Fungal | 0.0027 | 8 | 204 |
|  | 0.0056 | 8 | 99 |
|  | 0.014 | 8 | 46 |
|  | 0.027 | 8 | 28 |
|  | 0.056 | 8 | 20 |

The ferritin response of Ao-iron was compared to ferrous sulfate, the most widely used inorganic iron supplement. Despite ferrous sulfate being very absorbable by humans, it can also cause severe side effects in humans, especially in children. Because it is very reactive, ferrous sulfate added to food can cause food oxidation and as a result food develops off flavour and a short shelf life. Generally, ferrous sulfate supplements have been suggested to be taken with food. In contrast, iron in Ao-iron is in an organic form that can be taken without food. Using the ferritin response of ferrous sulfate as a control (100%) and comparing ferrous sulfate with corn meal, Ao-iron and Ao-iron with corn meal, the results show that Ao-iron was comparable to ferrous sulfate with corn (FIG. 5). The effect of corn meal on the ferritin response was more dramatic to ferrous sulfate than to Ao-iron. Also, Ao-iron is tasteless and can be added to food directly, but ferrous sulfate is mostly taken in a pill or capsule form. Despite that the ferritin response in Caco-2 Cell was 52% of the ferrous sulfate, but it was better than iron in beef and corn with 25% and less than 20% respectively.

Example 4

To produce a food grade iron supplement, *Aspergillus oryzae* ATCC 22787 was selected to grow in a media made of corn flour, soybean hulls and wheat bran. The corn flour and wheat bran were treated with enzymes of amylases, gluco-amylases, phytase. Initial mix of the total flour and bran in the media ranged from 10-25%. Amylase was added at neutral pH around 6 at temperature of 105-107° C. via autoclave or jet cooking, and then held at 95° C. for 2 hours. The next step is to apply gluco-amylase for saccharification. Finally, phytase may or may not needed to treat the mixture of corn and wheat bran at the temperature and pH required by the specification of the enzyme manufacturer. If soy bean hulls are used, the preferred practice would be to apply protease to the soybean hull in water at the pH required by the enzyme manufacturer. The protease with optimal pH at acid range is preferred. After the enzyme treatment, a mixture of these ingredients can be formed and used for both fungal pre-culture and product media. In a 14-L stir tank fermenter, a 48-72 hour fermentation at pH 4-6 and 28° C. was carried out as shown in FIG. 1. A filter made of double layers of nylon cloth was used to harvest the fungal biomas in the laboratory and product was dried in 60° C. in a oven for over night. The composition of final iron enriched product fungal is shown in Table 8.

TABLE 8

Composition (dry weight based) of Iron Enriched Fungal Product

| Test | Content |
|---|---|
| Moisture | 8.69% |
| Protein, crude | 29.8% |
| Fat, crude | 9.2% |
| Ash | 16.3% |
| Sulfur | 0.59% |
| Phosphorus | 2.28% |
| Potessium | 1.71% |
| Magnesium | 0.20% |
| Calcium | 0.07% |
| Iron | 37886 ppm or 3.79% |

In addition, the *Aspergillus oryzae* strain used is a non mycotoxin producing microorganism. The toxin tests by LC/MS/MS method by a commercial laboratory showed no detectable mycotoxins present (Table 9).

TABLE 9

Mycotoxin test results shown no toxin in the iron enriched fungal product.

| Analysis | Results |
|---|---|
| Aflatoxin B1 | Non at <10 ppb level |
| Aflatoxin B2 | Non at <10 ppb level |
| Aflatoxin G1 | Non at <10 ppb level |
| Aflatoxin G2 | Non at <10 ppb level |
| Fumonisin B1 | Non at <0.2 ppm level |
| Fumonisin B2 | Non at <0.2 ppm level |
| Fumonisin B3 | Non at <0.2 ppm level |
| Nivalenol | Non at <0.2 ppm level |
| Ochratoxin A | Non at <0.2 ppm level |
| Zearalenol | Non at <0.2 ppm level |
| Zearalenone | Non at <0.2 ppm level |

Example 5

Other inorganic minerals such as selenium and zinc have been used to produce selenium or zinc enriched yeast, but the use of filamentous fungi has not been reported. Both forms of enrichment provide better functional properties than the inorganic equivalents. A similar process (FIG. 2) was used for growing *Aspergillus oryzae* fortified with either sodium selenite or zinc sulfate. The dose of either inorganic salt was calculated as a concentration of the elements rather than the concentration of salt to enable comparison with the mineral content in the fungal biomass. Increases in the selected mineral contents in the fungal product are listed in Table 10 and demonstrate that *Aspergillus oryzae* can be used to produce organic selenium or zinc enriched products. However, as the dose of Se increased to 15 mg/L, the fungal yield significantly reduced. Zinc, however, increased fungal yield and over 67% of the added zinc element was converted to organic zinc.

TABLE 10

Production of Se or Zn enriched *Aspergillus oryzae* in corn-ethanol Syrup

|  | Dose mg/L | Mineral content mg/kg | Fungal Yield g/L |
|---|---|---|---|
| Sodium selenite, as Se | 0 | 1.5 | 16.99 |
|  | 1 | 11.7 | 29.32 |
|  | 2 | 20.05 | 27.22 |
|  | 3 | 31.4 | 28.07 |
|  | 5 | 47 | 19.88 |
|  | 15 | 180 | 16.36 |
| Zinc Sulfate, as Zn | 0 | 161 | 16.99 |
|  | 1000 | 28900 | 28.9 |

It will be appreciated by persons skilled in the art that numerous variations and/or modifications may be made to the technology as shown in the specific embodiments without departing from the spirit or scope of the technology as broadly described. The present embodiments are, therefore, to be considered in all respects as illustrative and not restrictive.

The invention claimed is:

1. A process for forming an iron supplement suitable for human consumption, the process comprising:
providing to a fermentation vessel a culture medium comprising an agricultural by-product or a food processing by-product, wherein inorganic iron salts or iron compounds selected from the group consisting of ferric sulfate, ferrous sulfate, ferric ammonium. citrate, ferrous citrate and EDTA iron are added to the media to provide at least 2,000 mg/L iron to the culture medium;
culturing filamentous fungi to accumulate iron in organic form in the cell wall of the filamentous fungi, wherein the filamentous fungi are selected from the group consisting of *Aspergillus oryzne* and *Aspergillus niger*, wherein the culturing is in the culture medium in the fermentation vessel for 48 to 72 hours; and
harvesting the filamentous fungi containing iron to form an iron supplement containing fungal biomass having at least 20,000 mg/kg iron in organic form.

2. The process according to claim 1 wherein the agricultural by-product is selected from the group consisting of corn process by-products, wheat process by-products, soybean process by-products, and combinations thereof.

3. The process according to claim 1 wherein the agricultural by-product is condensed corn syrup.

4. The process according to claim 1 wherein the food processing by-product is selected from the group consisting of corn steeping liquor, corn stillage, soybean whey, sugar cane and beet molasses, soybean hull, wheat bran, wheat hull, and combinations thereof.

5. The process according to claim 1 wherein the inorganic iron salts or iron compounds are ferric sulfate or ferrous sulfate.

6. The process according to claim 1 wherein the filamentous fungi biomass is harvested by filtration, centrifugation, or drying.

7. The process according to claim 6 wherein the filamentous fungi biomass is harvested by drying at a temperature lower than 90° C.

8. The process according to claim 1 wherein the iron supplement contains from 20,000 to 40,000 mg/kg iron.

9. The process according to claim 8 wherein the iron supplement contains 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, or 40,000 mg/kg iron.

10. The process according to claim 1 wherein the iron supplement further contains diluents.

11. The process according to claim 1 wherein the iron supplement further contains co-ingredients selected from selenium and zinc.

12. The process according to claim 11 wherein the iron supplement further contains selenium from 10 to 400 mg/kg, or zinc from 20 to 20000 20,000 mg/kg, or selenium from 10 to 400 mg/kg and zinc from 2.0 to 20,000 mg/kg.

13. The process according to claim 1 wherein the filamentous fungi is Aspergillus oryzae.

14. The process according to claim i wherein the filamentous fungi is cultured at room temperature or elevated temperatures from 25 to 55° C.

15. The process according to claim 1 wherein the filamentous fungi is cultured at a temperature of 28 to 30° C.

16. The process according to claim 1 wherein the culture is agitated or stirred during fermentation in the fermentation vessel.

* * * * *

UNITED STATES PATENT AND TRADEMARK OFFICE
CERTIFICATE OF CORRECTION

| | |
|---|---|
| PATENT NO. | : 11,478,519 B2 |
| APPLICATION NO. | : 16/557293 |
| DATED | : October 25, 2022 |
| INVENTOR(S) | : J. Bruce Wicking |

It is certified that error appears in the above-identified patent and that said Letters Patent is hereby corrected as shown below:

In the Claims

In Column 14, beginning Line 35, Claim 12 should read as follows:
12. The process according to claim 15 wherein the iron supplement further contains selenium from 10 to 400 mg/kg, or zinc from 20 to 20,000 mg/kg, or selenium from 10 to 400 mg/kg and zinc from 20 to 20,000 mg/kg.

Signed and Sealed this
Eighteenth Day of July, 2023

Katherine Kelly Vidal
*Director of the United States Patent and Trademark Office*